(12) United States Patent
Iketaki et al.

(10) Patent No.: US 10,558,028 B2
(45) Date of Patent: Feb. 11, 2020

(54) SUPER-RESOLUTION MICROSCOPE

(71) Applicants: OLYMPUS CORPORATION, Hachioji-shi, Tokyo (JP); UNIVERSITY OF TSUKUBA, Tsukuba-shi, Ibaraki (JP)

(72) Inventors: Yoshinori Iketaki, Tokyo (JP); Hideaki Kanou, Tsukuba (JP)

(73) Assignees: OLYMPUS CORPORATION, Tokyo (JP); UNIVERSITY OF TSUKUBA, Tsukuba-shi (JP)

( * ) Notice: Subject to any disclaimer, the term of this patent is extended or adjusted under 35 U.S.C. 154(b) by 0 days.

(21) Appl. No.: 16/206,075

(22) Filed: Nov. 30, 2018

(65) Prior Publication Data

US 2019/0196166 A1 Jun. 27, 2019

(30) Foreign Application Priority Data

Dec. 26, 2017 (JP) ................................ 2017-249738

(51) Int. Cl.
*G02B 21/16* (2006.01)
*G02B 21/02* (2006.01)
(Continued)

(52) U.S. Cl.
CPC ......... *G02B 21/16* (2013.01); *G01N 21/6458* (2013.01); *G02B 21/02* (2013.01); *G02B 21/086* (2013.01)

(58) Field of Classification Search
CPC .. G01N 21/636; G01N 21/6458; G02B 21/02; G02B 21/086; G02B 21/16
See application file for complete search history.

(56) References Cited

U.S. PATENT DOCUMENTS

| 6,667,830 | B1 | 12/2003 | Iketaki et al. | |
| 7,304,315 | B2 | 12/2007 | Iketaki et al. | |
| 2001/0045529 | A1* | 11/2001 | Iketaki | .................. G01J 3/4406 250/493.1 |

FOREIGN PATENT DOCUMENTS

| JP | 2001100102 A | 4/2001 |
| JP | 2010015026 A | 1/2010 |
| WO | 2005038441 A1 | 4/2005 |

OTHER PUBLICATIONS

Nandor Bokor, et al., "New Design Method for a Phase Plate in Super-Resolution Fluorescence Microscopy," Applied Spectroscopy, vol. 68, No. 3, 2014, pp. 353-361.

(Continued)

*Primary Examiner* — Mark R Gaworecki
(74) *Attorney, Agent, or Firm* — Holtz, Holtz & Volek PC (57) ABSTRACT

A super-resolution microscope includes an illuminator and a detector. The illuminator irradiates illumination beams of different wavelengths through an objective lens onto a sample while causing at least a portion of the illumination beams to overlap spatially and temporally. The detector detects a signal beam generated by the sample as a result of irradiation of the sample with the illumination beams. The illumination beams include a first illumination beam that induces a first nonlinear optical process with respect to the sample and a second illumination beam that induces a second nonlinear optical process that suppresses the first nonlinear optical process. The nonlinear susceptibility of the second nonlinear optical process is greater than the nonlinear susceptibility of the first nonlinear optical process.

11 Claims, 8 Drawing Sheets

(51) Int. Cl.
*G02B 21/08* (2006.01)
*G01N 21/64* (2006.01)

(56) References Cited

OTHER PUBLICATIONS

Takeshi Watanabe, et al., "Formation of a doughnut laser beam for super-resolving microscopy using a phase spatial light modulator," Opt. Eng., 43(5), May 2004, pp. 1136-1143.
Takeshi Watanabe, et al., "Generation of a doughnut-shaped beam using a spiral phase plate," Review of Scientific Instruments, vol. 75, No. 12, Dec. 2004, pp. 5131-5135.
Yasuyuki Ozeki, et al., "Stimulated Raman scattering microscope with shot noise limited sensitivity using subharmonically synchronized laser pulses," Optics Express, vol. 18, No. 13, Jun. 21, 2010, pp. 13708-13719.
Yoshinori Iketaki, "Three-Dimensional Super-Resolution Microscope Using Two-Color Annular Phase Plate," Applied Physics Express 3, 2010, pp. 085203-1 to 085203-3.

\* cited by examiner

SUPER-RESOLUTION MICROSCOPE

CROSS-REFERENCE TO RELATED APPLICATION

The present application claims priority to and the benefit of Japanese Patent Application No. 2017-249738 filed Dec. 26, 2017, the entire contents of which are incorporated herein by reference.

TECHNICAL FIELD

The present disclosure relates to a super-resolution microscope.

BACKGROUND

A known example of a super-resolution microscope is a fluorescence microscope that allows observation, at a high spatial resolution exceeding the diffraction limit, of a sample including molecules that have at least two or more excited quantum states (for example, see patent literature (PTL) 1 and 2).

With the molecules in the sample in a stable state, the fluorescence microscope disclosed in PTL 1 and PTL 2 spatially scans the sample surface with a fluorescence spot that is shrunk to the diffraction limit or lower, for example using a combination of pump light for excitation from a ground state to a first quantum state and erase light for causing molecules to transition further to another quantum state. A fluorescence image with resolution exceeding the spatial resolution at the diffraction limit is then obtained by two-dimensionally arranging the fluorescence signal at each measurement point and performing image processing on a computer.

As a representative example, the pump light is irradiated onto a sample including fluorophores, and the fluorophores are excited to a first quantum state. The molecules in the first quantum state are quenched by further irradiating the sample with the erase light to force the fluorophores to transition to another quantum state. As a result, fluorescence relaxation from the first quantum state is controlled. By the sample being simultaneously irradiated by pump light and a hollow erase light with an objective lens, the fluorescence spot formed on the sample surface that is dyed with fluorescent dye is shrunk to the diffraction limit or lower, leaving behind the central portion.

CITATION LIST

Patent Literature

PTL JP2001100102A
PTL 2: JP201015026A

SUMMARY

To this end, a super-resolution microscope according to the present disclosure includes an illuminator and a detector. The illuminator irradiates a plurality of illumination beams of different wavelengths through an objective lens onto a sample while causing at least a portion of the plurality of illumination beams to overlap spatially and temporally. The detector detects a signal beam generated by the sample as a result of irradiation of the sample with the plurality of illumination beams. The plurality of illumination beams include a first illumination beam that induces a first nonlinear optical process with respect to the sample and a second illumination beam that induces a second nonlinear optical process that suppresses the first nonlinear optical process. The nonlinear susceptibility of the second nonlinear optical process is greater than the nonlinear susceptibility of the first nonlinear optical process.

The second illumination beam may have a shorter wavelength than the first illumination beam.

The first illumination beam and the second illumination beam may have different intensity distributions on a converging surface of the objective lens.

The second illumination beam may have a minimum in the intensity distribution on the converging surface.

The first illumination beam may have a maximum in the intensity distribution on the converging surface.

Each of the first nonlinear optical process and the second nonlinear optical process may include any of a second-order nonlinear optical process, a third-order nonlinear optical process, a fourth-order nonlinear optical process, and a fifth-order nonlinear optical process.

The second-order nonlinear optical process may be any of second harmonic generation (SHG), sum frequency generation (SFG), difference frequency generation (DFG), and an optical parametric process.

The third-order nonlinear optical process may be any of third harmonic generation (THG), third-order sum frequency generation (TSFG), coherent anti-Stokes Raman scattering (CARS), stimulated Raman scattering (SRS) (stimulated Raman gain (SRG), stimulated Raman loss (SRL)), optical Kerr effect (OKE), Raman induced Kerr effect (RIKE), stimulated Rayleigh scattering, stimulated Brillouin scattering (SBS), stimulated Kerr scattering, stimulated Rayleigh-Bragg scattering, stimulated Mie scattering, self phase modulation (SPM), cross phase modulation (XPM), two-photon absorption, optical-field induced birefringence, and electric-field induced SHG.

The fourth-order nonlinear optical process may be four-wave mixing (FWM).

The fifth-order nonlinear optical process may be any of two-photon excitation fluorescence (TPEF), hyper-Raman scattering, hyper-Rayleigh scattering, and coherent anti-Stokes hyper-Raman scattering.

The first illumination beam and the second illumination beam may be coherent beams.

The illuminator may include a spatial modulator configured to modulate a phase or a spatial distribution of an electrical field vector of the second illumination beam.

The maximum of the first illumination beam and the minimum of the second illumination beam may overlap coaxially at the converging surface.

The detector may detect forward scattered light, or light generated in a nonlinear optical process, from the sample as the signal beam.

The second nonlinear optical process may include a lower order nonlinear optical process than the first nonlinear optical process.

The first illumination beam may include illumination beams of at least two colors of different wavelengths.

BRIEF DESCRIPTION OF THE DRAWINGS

In the accompanying drawings.

DETAILED DESCRIPTION

With a known super-resolution microscope, a sample needs to be dyed with fluorophores. Therefore, in particular when observing a live biological sample, the dye molecules affect the metabolism and the like of the biological sample, which may make it impossible to observe the natural biological phenomena of the biological sample. The present disclosure provides a super-resolution microscope that allows a sample to be observed at a spatial resolution exceeding the diffraction limit without dying.

Embodiments of the present disclosure are described below with reference to the drawings.

In an embodiment of the present disclosure, a second nonlinear optical process is forcefully induced at the same time as a first nonlinear optical process, and the intensity of a signal beam generated by the first nonlinear optical process is partially suppressed by the second nonlinear optical process. To this end, the illumination beam (stimulation beam) that induces the first nonlinear optical process and quench light that induces the second nonlinear optical process, for example, are irradiated onto the sample coaxially. The stimulation beam at this time is concentrated on the sample as a Gaussian spot having an intensity peak at the optical axis center. On the other hand, the quench light is concentrated on the sample in a shape having an intensity local minimum value along the optical axis.

In this case, the first nonlinear optical process is suppressed in a region in which the stimulation beam and the quench light overlap. Consequently, the region that generates a signal beam is at the optical axis central portion and is a smaller spot than the diffraction limit. Spatially scanning the sample with this spot, therefore, allows the sample to be observed at a spatial resolution exceeding the diffraction limit.

The condition necessary for improving the spatial resolution is that generation of a signal beam in the region where the stimulation beam and the quench light overlap be suppressed reliably and efficiently.

The signal beam (intensity) generated by the nonlinear optical process at a certain time and a certain point is given by the macroscopic polarization in the sample medium represented by Expression (1) below (for example, see the Spectroscopial Society of Japan, Measurement Technique Series, "Nonlinear Optical Measurement", edited by Takayoshi Kobayashi, Scientific Societies Press Ltd., first printing Dec. 20, 1996).

$$\overrightarrow{p(\vec{r}, t)}^{(NL)} = \tag{1}$$

$$\sum_{m=1}^{\infty} \int x^{m+1}(\vec{r} - \vec{r}_1, \vec{r} - \vec{r}_2, \Lambda, \vec{r} - \overrightarrow{r_{m+1}}, t - t_1, t - t_2, \Lambda, t - t_{m+1})$$

$$\vec{E}_1(\vec{r}_1, t_1)\vec{E}_2(\vec{r}_2, t_2)\Lambda \overrightarrow{E_m(r_{m+1}}, t_{m+1})d\vec{r}_1 d\vec{r}_2 \Lambda \overrightarrow{dr_{m+1}} dt_1 dt_2 \Lambda d_m$$

In Expression (1), t is time, and $\vec{r}$ is a point (position). $\vec{E}_m(\vec{r}_m, t_m)$ indicates the electric field at time $t_m$, position $\vec{r}_m$ of the $m^{th}$ illumination beam. $x^{m+1}(\vec{r}-\vec{r}_1, \vec{r}-\vec{r}_2, \Lambda, \vec{r}-\vec{r}_{m+1}, t-t_1, t-t_2, \Lambda, t-t_{m+1})$ indicates the $(nn+1)^{th}$ nonlinear susceptibility (electric susceptibility). For example, $x^2(\vec{r}-\vec{r}_1, \vec{r}-\vec{r}_2, t-t_1, t-t_2)$ indicates the second-order nonlinear susceptibility, and $x^3(\vec{r}-\vec{r}_1, \vec{r}-\vec{r}_2, \vec{r}-\vec{r}_3, t-t_1, t-t_2, t-t_3)$ indicates the third-order nonlinear susceptibility.

From Expression (1), the signal beam yielded by a second-order nonlinear optical process in which two different wavelengths are involved is represented by Expression (2) below.

$$\overrightarrow{p(\vec{r}, t)}^{(2)} = \tag{2}$$

$$\int x^2(\vec{r} - \vec{r}_1, \vec{r} - \vec{r}_2, t - t_1, t - t_2)\vec{E}_1(\vec{r}_1, t_1)\vec{E}_2(\vec{r}_2, t_2)d\vec{r}_1 d\vec{r}_2 dt_1 dt_2$$

In Expression (2), $\vec{E}_1(\vec{r}_1, t_1)$ corresponds to an electric field with a wavelength $\lambda_1$, and $\vec{E}_2(\vec{r}_2, t_2)$ corresponds to an electric field with a wavelength $\lambda_2$.

Similarly, the signal beam yielded by a third-order nonlinear optical process in which wavelengths of three colors are involved, for example, is represented by Expression (3) below.

$$\overrightarrow{p(\vec{r}, t)}^{(3)} = \int x^3(\vec{r} - \vec{r}_1, \vec{r} - \vec{r}_2, \vec{r} - \vec{r}_3, t - t_1, t - t_2, t - t_3) \tag{3}$$

$$\vec{E}_1(\vec{r}_1, t_1)\vec{E}_2(\vec{r}_2, t_2)\vec{E}_3(\vec{r}_3, t_3)d\vec{r}_1 d\vec{r}_2 d\vec{r}_3 dt_1 dt_2 dt_3$$

In Expression (3), $\vec{E}_1(\vec{r}_1, t_1)$ corresponds to an electric field with a wavelength $\lambda_1$, $\vec{E}_2(\vec{r}_2, t_2)$ corresponds to an electric field with a wavelength $\lambda_2$, and $\vec{E}_3(\vec{r}_3, t_3)$ corresponds to an electric field with a wavelength $\lambda_3$.

The polarization in which only $\vec{E}_1(\vec{r}_1, t_1)$ and $\vec{E}_2(\vec{r}_2, t_2)$ are involved among the wavelengths of three different colors is represented by Expression (4) below and is classified as a third-order nonlinear optical process.

$$\overline{p(\vec{r},t)^{(3)}} = \qquad (4)$$

$$\int \chi^3(\vec{r}-\vec{r}_1, \vec{r}-\vec{r}_2, t-t_1, t-t_2)\vec{E}_1(\vec{r}_1, t_1)\left[\vec{E}_2(\vec{r}_2, t_2)\right]^2 d\vec{r}_1 d\vec{r}_2 dt_1 dt_2$$

Similarly, the case of only $\vec{E}_1(\vec{r}_1, t_3)$ being involved and the illumination beam being proportional to the cube of the electric field is represented by Expression (5) below and is classified as a third-order nonlinear optical process.

$$\overline{p(\vec{r},t)^{(3)}} = \int \chi^3(\vec{r}-\vec{r}_1, t-t_1)\left[\vec{E}_1(\vec{r}_1, t_1)\right]^3 d\vec{r}_1 dt_1 \qquad (5)$$

In an embodiment of the present disclosure, illumination beams of a plurality of wavelengths are concentrated on a sample, a plurality of nonlinear optical processes are simultaneously induced, a response signal yielded by a first nonlinear optical process (signal generation process) selected from among the plurality of nonlinear optical processes is designated as a signal beam, and this signal beam is suppressed by a second nonlinear optical process (suppression process), which is another process. At this time, the following Expression is satisfied to allow the suppression process to be induced more efficiently than the signal generation process:

$$x_q > x_s \qquad (6)$$

where $x_q$ is the nonlinear susceptibility of the suppression process, and $x_s$ is the nonlinear susceptibility of the signal generation process.

It is known from the theory of nuclear physics that the nonlinear susceptibility decreases as the order increases. Specifically, the second-order nonlinear susceptibility $x^2$ is on the order of $10^{-7}$ esu, and the third-order nonlinear susceptibility $x^3$ is on the order of $10^{-14}$ esu. Furthermore, the fifth-order nonlinear susceptibility $x^5$ is on the order of $10^{-21}$ esu. The nonlinear susceptibility continues to decrease by orders of magnitude each time the order increases. Accordingly, use of a lower order nonlinear optical process in the suppression process than in the signal generation process can typically be considered effective.

Even for the same order, however, the nonlinear susceptibility differs greatly depending on the vibrational level of the molecules involved. For example, in the same third-order coherent anti-Stokes Raman scattering (CARS) process, the nonlinear susceptibility is known to be an order of magnitude greater for a CH group than a C=C group in the molecular fingerprint region.

In this case, generation of a signal beam can be effectively suppressed with low-intensity quench light by using a CARS process in which a CH group is involved in the suppression process and using a CARS process in which a C=C group is involved in the signal generation process. A high-frequency CH group and OH group typically have an increased nonlinear susceptibility in the fingerprint region of a low-frequency molecule when a CARS process is used, making these groups suitable for the suppression process.

Typically, the nonlinear susceptibility increases closer to the absorption edge that accompanies electron transition due to visible light or ultraviolet light. Use of a high-frequency nonlinear optical process in the suppression process is therefore advantageous in the case of suppressing response light in a process of the same order.

In an embodiment of the present disclosure, a CARS process of a molecular fingerprint region that can provide abundant information by chemical composition analysis is used. The CARS process is a representative third-order nonlinear optical process that has been the most widely used vibrational spectroscopy technique in recent years. In particular, numerous fine absorptions in the molecular fingerprint region (wavenumber of 1300 to 650 cm$^{-1}$) are observed, and the pattern thereof is unique to a substance. A substance can therefore be identified by comparing the absorption in this region with known materials or a spectral database.

Specifically, the CARS beam of a CARS process in the molecular fingerprint region is designated as a signal beam, and this signal beam is suppressed by induction of a separate CARS process. In greater detail, when these CARS processes compete, the CARS process derived from an OH group that has a high signal generation efficiency is designated as the suppression process.

In the CARS process, two laser beams ($\omega_1$ beam, $\omega_2$ beam) with different angular frequencies are typically used. If the difference in angular frequency $\omega_1 - \omega_2$ between these two incident beams matches the angular frequency of the vibration mode of the sample molecule, then the vibration mode of multiple sample molecules is simultaneously excited.

The molecular vibration (vibration coherence) generated in this way is extracted as an $\omega_{CARS}$ beam (CARS beam) derived from third-order nonlinear polarization by production of a sum frequency beam through the interaction between the molecule and a third laser beam ($\omega_3$ beam). In the CARS process, the condition $\omega_{CARS} = \omega_1 - \omega_2 + \omega_3$ is satisfied by the law of conservation of energy. Furthermore, the CARS beam is generated in the direction $k_{CARS} = k_1 - k_2 + k_3$ by a phase matching condition. Here, $k_x$ is a wavenumber vector of the $\omega_x$ beam.

In the CARS process, the $\omega_1$ beam is often used as the $\omega_3$ beam. In other words, the CARS process is induced with two colors, the $\omega_1$ beam and the $\omega_2$ beam, to generate a signal beam from the CARS beam with an angular frequency of $(2\omega_1 - \omega_2)$. That is, the signal intensity of the $\omega_{CARS}$ beam increases nonlinearly with respect to the intensity of the $\omega_1$ beam. Raman scattered light (CARS beam) with good directionality can be obtained by the CARS process from the phase matching condition. In particular, since the forward scattered light is characteristically intense, an image can be acquired at a fast measurement rate.

The CARS process is excellent in that it detects scattered light caused by the vibrational level of a molecule that is to be observed, thereby allowing detection of the existence of the molecule without performing dyeing. This process is convenient for detecting biological molecules of a biological sample in its natural state, without subjecting the live sample to chemical treatment.

First Embodiment

Figure 1:
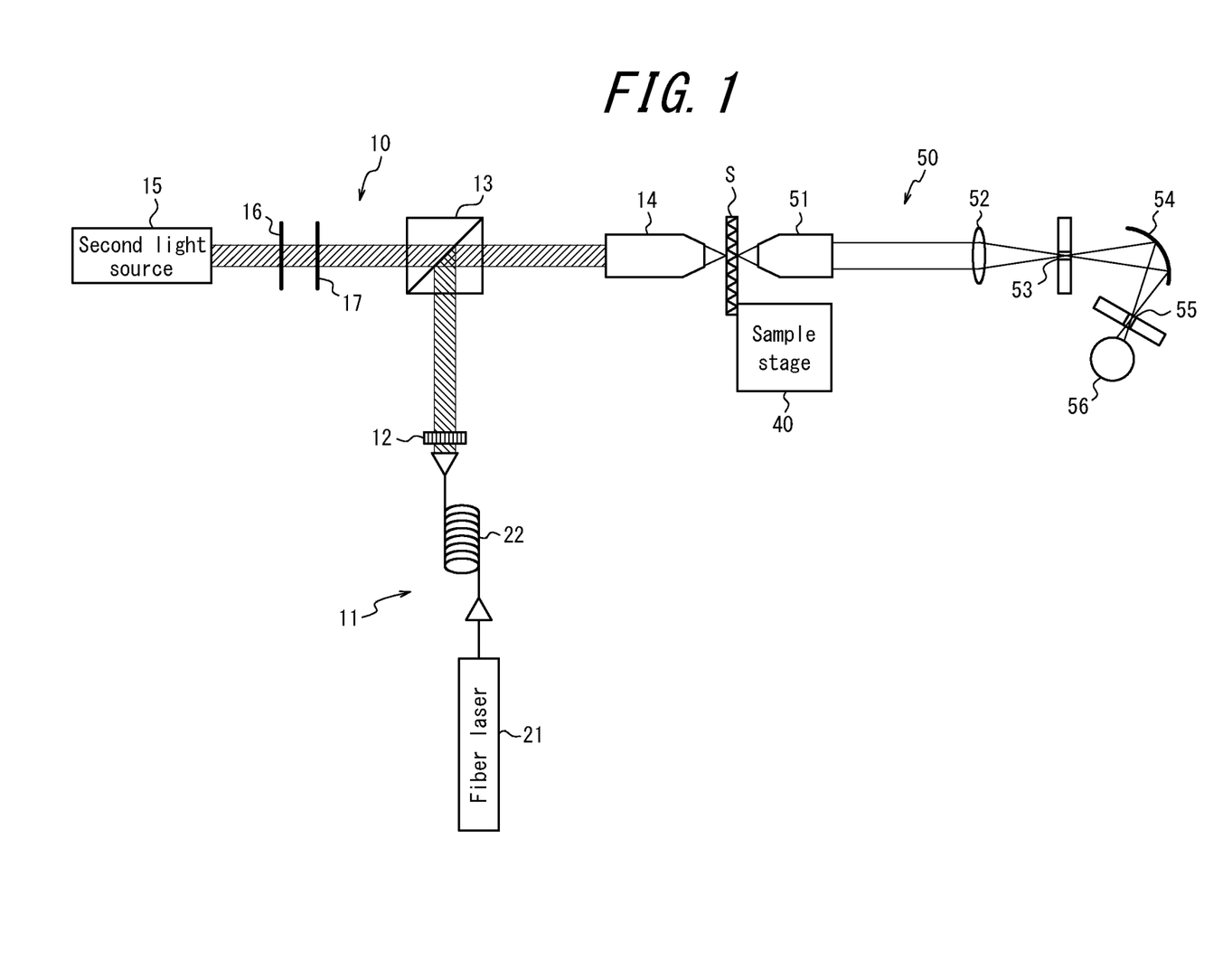
FIG. 1 illustrates the schematic configuration of a super-resolution microscope according to a first embodiment.

FIG. 1 illustrates the schematic configuration of a super-resolution microscope according to the first embodiment of the present disclosure. The super-resolution microscope illustrated in FIG. 1 constitutes a CARS microscope and includes an illuminator 10 and a detection unit 50. In the present embodiment, the CARS beam derived from the band of the "molecular fingerprint region" existing near a wavenumber of 1000 cm$^{-1}$, for example, is designated as a signal beam. A CARS process derived from an OH group existing near a wavenumber of 3200 cm$^{-1}$, for example, is used in the suppression process.

The illuminator 10 includes a first light source 11, a multi-bandpass filter 12, a beam combiner 13, an objective lens 14, a second light source 15, a quarter-wave plate 16, and a spatial modulator 17.

The first light source 11 includes one super continuum light source. A coherent $\omega_1$ beam and $\omega_2$ beam that become a first illumination beam are generated from the light emitted from the super continuum light source. The super continuum light source 11 includes, for example, a fiber laser 21 that emits 1064 nm wavelength femtosecond pulsed light and a photonic crystal fiber 22 that emits a white laser beam with the beam emitted by the fiber laser 21 as a seed beam.

The white laser beam emitted from the photonic crystal fiber 22 is incident on the multi-bandpass filter 12, and the $\omega_1$ beam and $\omega_2$ beam are extracted spectrally. In the present embodiment, 1190 nm wavelength light is used as the $\omega_1$ light, and 1064 nm wavelength seed light incident on the photonic crystal fiber 22 from the fiber laser 21 is used as the $\omega_2$ light.

The $\omega_1$ beam and the $\omega_2$ beam extracted from the multi-bandpass filter 12 pass through the beam combiner 13, are incident on the objective lens 14, and are focused on the sample S. Here, the $\omega_1$ beam and the $\omega_2$ beam focused on the sample S are a Gaussian beam and have a maximum value in the intensity distribution on the converging surface. As a result, the signal generation process is induced, and a CARS beam stemming from the "molecular fingerprint region" of a particular organic molecule in the sample S is selectively induced.

The second light source 15 emits an $\omega_q$ beam as a second illumination beam (quench light) that suppresses induction of the CARS process. For example, a Ti sapphire laser, which is a variable wavelength femtosecond laser, is used in the second light source 15. Coherent light with a wavelength of 794 nm (wavenumber of 12598 cm$^{-1}$) is used as the quench light. The quench light emitted from the second light source 15 is converted to a circularly polarized beam by the quarter-wave plate 16, subsequently passes through the spatial modulator 17 and is incident on the beam combiner 13, is combined coaxially with the first illumination beam ($\omega_1$ beam, $\omega_2$ beam), and is focused on the sample S by the objective lens 14.

Figure 2:
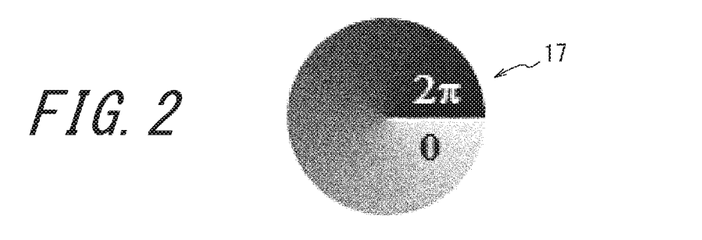
FIG. 2 illustrates the schematic configuration of a first example of a spatial modulator.
Figure 3:
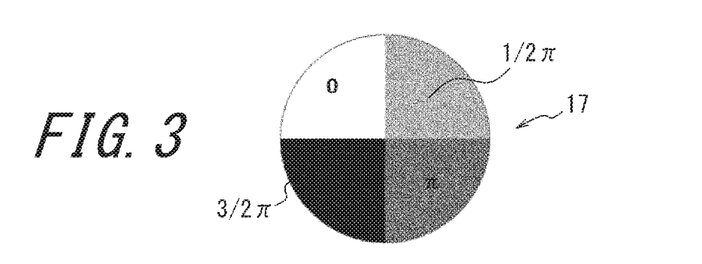
FIG. 3 illustrates the schematic configuration of a second example of a spatial modulator.

The spatial modulator 17 is, for example, configured as illustrated in FIG. 2 or FIG. 3. The spatial modulator 17 illustrated in FIG. 2 continuously changes the phase of the quench light from 0 to $2\pi$ (or an integer multiple thereof) over one revolution centering on the optical axis. The spatial modulator 17 illustrated in FIG. 3 includes four independent regions around the optical axis and changes the phase of the quench light in steps of $\pi/2$ (or an integer multiple thereof) from 0 to $2\pi$ (or an integer multiple thereof) centering on the optical axis.

Upon the quench light passing through the spatial modulator 17 in FIG. 2 or FIG. 3, the phase of the quench light is inverted between points symmetrical about the optical axis. Accordingly, upon the quench light being focused with the objective lens 14, a hollow beam spot that has a minimum in the intensity distribution is formed on the converging surface (for example, see "Formation of a doughnut laser beam for super-resolving microscopy using a phase spatial light modulator", T. Watanabe, Y. Igasaki, N. Fukuchi, M. Sakai, S. Ishiuchi, M. Fujii, T. Omatsu, K. Yamamoto and Y. Iketaki, Opt. Eng., 43(2004) 1136).

Figure 4:
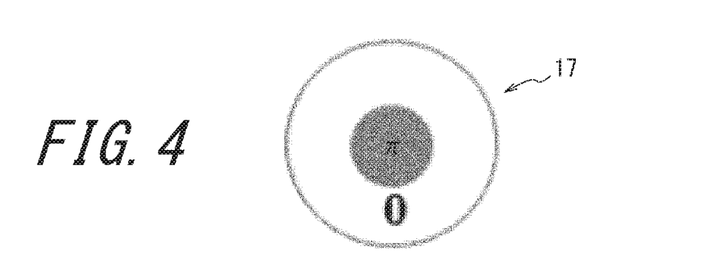
FIG. 4 illustrates the schematic configuration of a third example of a spatial modulator.
Figure 5:
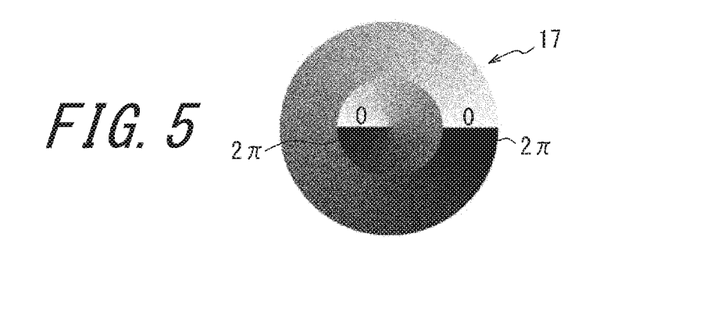
FIG. 5 illustrates the schematic configuration of a fourth example of a spatial modulator.

The spatial modulator 17 may, for example, be configured as illustrated in FIG. 4 or FIG. 5. The spatial modulator 17 illustrated in FIG. 4 has a plurality (two in FIG. 4) of concentric (annular) regions centering on the optical axis of the quench light and inverts the sign of the phase of the quench light in the radial direction between adjacent regions. As in FIG. 4, the spatial modulator 17 illustrated in FIG. 5 inverts the sign of the phase of the quench light in the radial direction between adjacent concentric regions and also changes the phase of the quench light within each region from 0 to $2\pi$ or an integer multiple thereof over one revolution centering on the optical axis, as in FIG. 2.

Upon the quench light passing through the spatial modulator 17 illustrated in FIG. 4 or FIG. 5, the phase of the quench light is inverted in the radial direction. Therefore, upon this quench light being focused with the objective lens 14, a hollow beam spot that has a minimum in the intensity distribution on the converging surface is formed, as in the case of FIG. 2 and FIG. 3. Furthermore, the electrical field of the quench light is three-dimensionally offset in this case, thereby generating a three-dimensional microspace, located only at and around the focal point, where no light reaches (for example, see WO2005038441A1).

Figure 6:
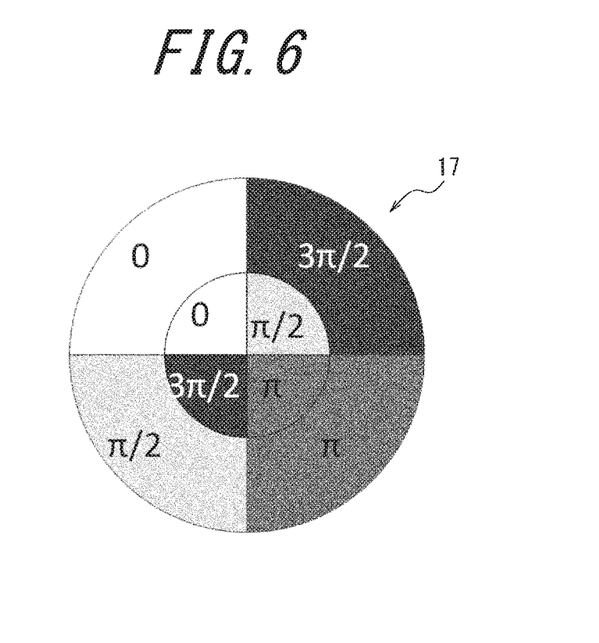
FIG. 6 illustrates the schematic configuration of a fifth example of a spatial modulator.
Figure 7:
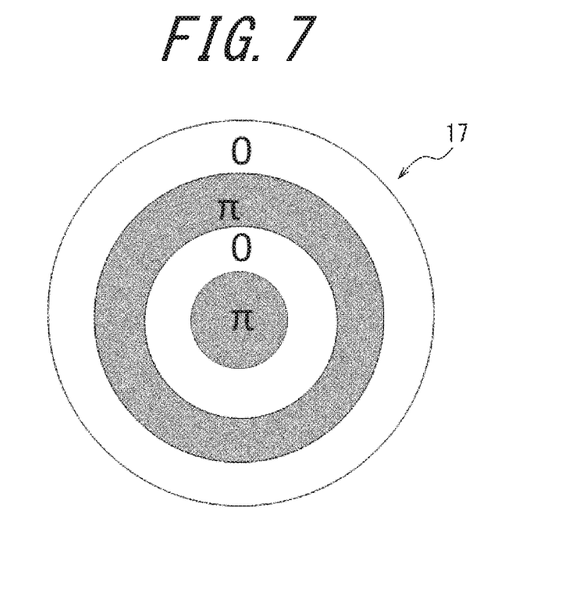
FIG. 7 illustrates the schematic configuration of a sixth example of a spatial modulator.

Alternatively, the spatial modulator 17 may be a phase plate or a wavelength plate that has the characteristics of FIG. 3 in each of a central portion and an annular portion, as illustrated in FIG. 6. Furthermore, the spatial modulator 17 may be a phase plate or a wavelength plate that has a multiple ring structure in which the phase of the quench light changes in each annular region from the central portion towards the outer annular portions, as illustrated in FIG. 7.

The spatial modulators 17 illustrated in FIG. 2 through FIG. 7 have a simple structure and can, for example, be produced with an optical thin film, with etching, or the like (for example, see "Three-dimensional super-resolution microscope using two-color annular phase plate", Y. Iketaki, Appl. Phys. Express, 3 (2010) 085203; "New Design Method for a Phase Plate in Super-Resolution Fluorescence Microscopy", N. Bokor and Y. Iketaki, Appl. Spectroscopy. 68(2014) 353; "Generation of a doughnut-shaped beam using a spiral phase plate", T. Watanabe, M. Fujii, Y. Watanabe, N. Nobuhito and Y. Iketaki, Rev. Sci. Instrum. 75(2004) 5132).

Figure 8:
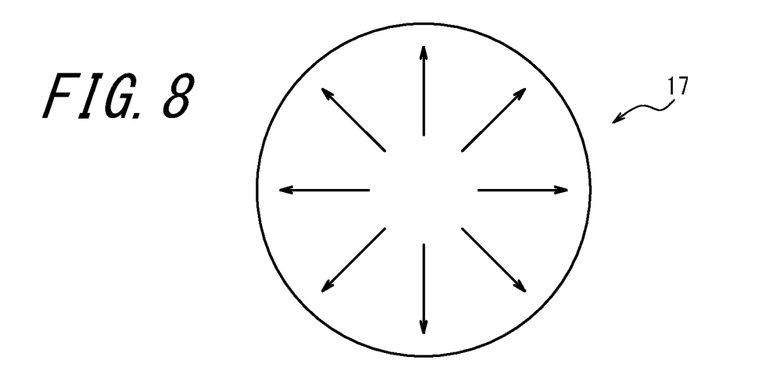
FIG. 8 illustrates the schematic configuration of a seventh example of a spatial modulator.
Figure 9:
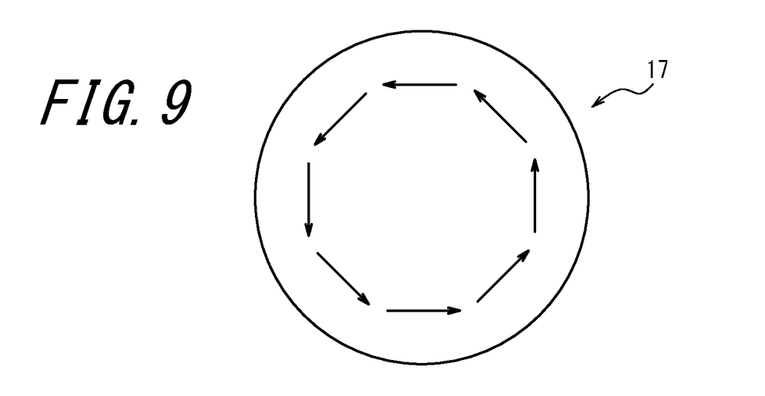
FIG. 9 illustrates the schematic configuration of an eighth example of a spatial modulator.
Figure 10:
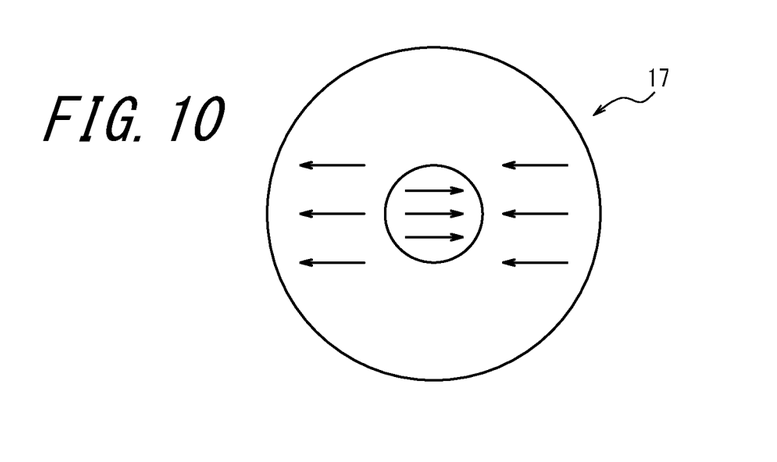
FIG. 10 illustrates the schematic configuration of a ninth example of a spatial modulator.

The spatial modulator 17 is not limited to the above-described case of modulating the phase of the quench light. A hollow beam spot that has a minimum in the intensity distribution on the converging surface can similarly be formed by modulating the polarization of the quench light. FIG. 8 through FIG. 10 schematically illustrate the configuration of spatial modulators 17 that modulate the polarization of the quench light. The spatial modulators 17 illustrated in FIG. 8 and FIG. 9 are configured to invert the direction of the electrical field vector of the quench light at positions symmetrical about the optical axis. The spatial modulator 17 illustrated in FIG. 10 has a plurality (two in FIG. 10) of concentric regions centered on the optical axis of the quench light and inverts the direction of the electrical field vector of the quench light between adjacent regions. The spatial modulators 17 in FIG. 8 through FIG. 10 can easily be produced by adhering waveplates together.

In FIG. 1, the sample S is mounted on a sample stage 40 that can be displaced three-dimensionally, i.e. in the z-direction along the optical axis of the objective lens 14 and in the x-direction and the y-direction that are orthogonal to each other in a plane orthogonal to the z-direction.

The detection unit 50 includes a collector lens 51, a focusing lens 52, a confocal pinhole 53, a spectroscope 54, a spectroscope slit 55, and a detector 56. The detector 56 is, for example, constituted by a photomultiplier, a semiconductor detector, or the like. The collector lens 51 is struck by forward scattered light of the sample S and converts the light to a parallel beam. The forward scattered light converted to a parallel beam by the collector lens 51 is focused by the focusing lens 52, passes through the confocal pinhole 53, and is incident on the spectroscope 54. The parallel beam is then split by the spectroscope 54, and a CARS beam (signal beam) of a desired wavelength component is extracted by the spectroscope slit 55 and detected by the detector 56. Here, the confocal pinhole 53 does not only function as a spatial filter but also functions to improve the monochromaticity of the CARS beam.

In the aforementioned structure, a CARS beam can be induced at super-resolution when the $\omega_1$ beam, the $\omega_2$ beam, and the quench light are overlapped spatially and temporally and focused on the sample S by the objective lens 14. In other words, since the CARS process due to the $\omega_1$ beam and the $\omega_2$ beam is inhibited at the annular portion of the quench light that is focused to be hollow, the region where the CARS beam is generated becomes smaller than the diffraction limit-sized focused spot of the $\omega_1$ beam and the $\omega_2$ beam.

Accordingly, by spatially scanning the sample S against the $\omega_1$ beam, the $\omega_2$ beam, and the quench light, the CARS beam can be imaged from the sample S at a spatial resolution exceeding the diffraction limit. Specifically, while spatially scanning the sample stage 40, the CARS signal detected by the detector 56 from the sample S is mapped. For example, a super-resolution microscopic image can be obtained by planar scanning. Since the confocal pinhole 53 is provided in the present embodiment, the three-dimensional super-resolution microscopic image can be obtained by spatially scanning in the xy-directions while displacing the sample stage 40 in the z-direction. In other words, the present embodiment can provide a super-resolution microscope that allows a sample to be observed at a spatial resolution exceeding the diffraction limit without dying.

Figure 11:
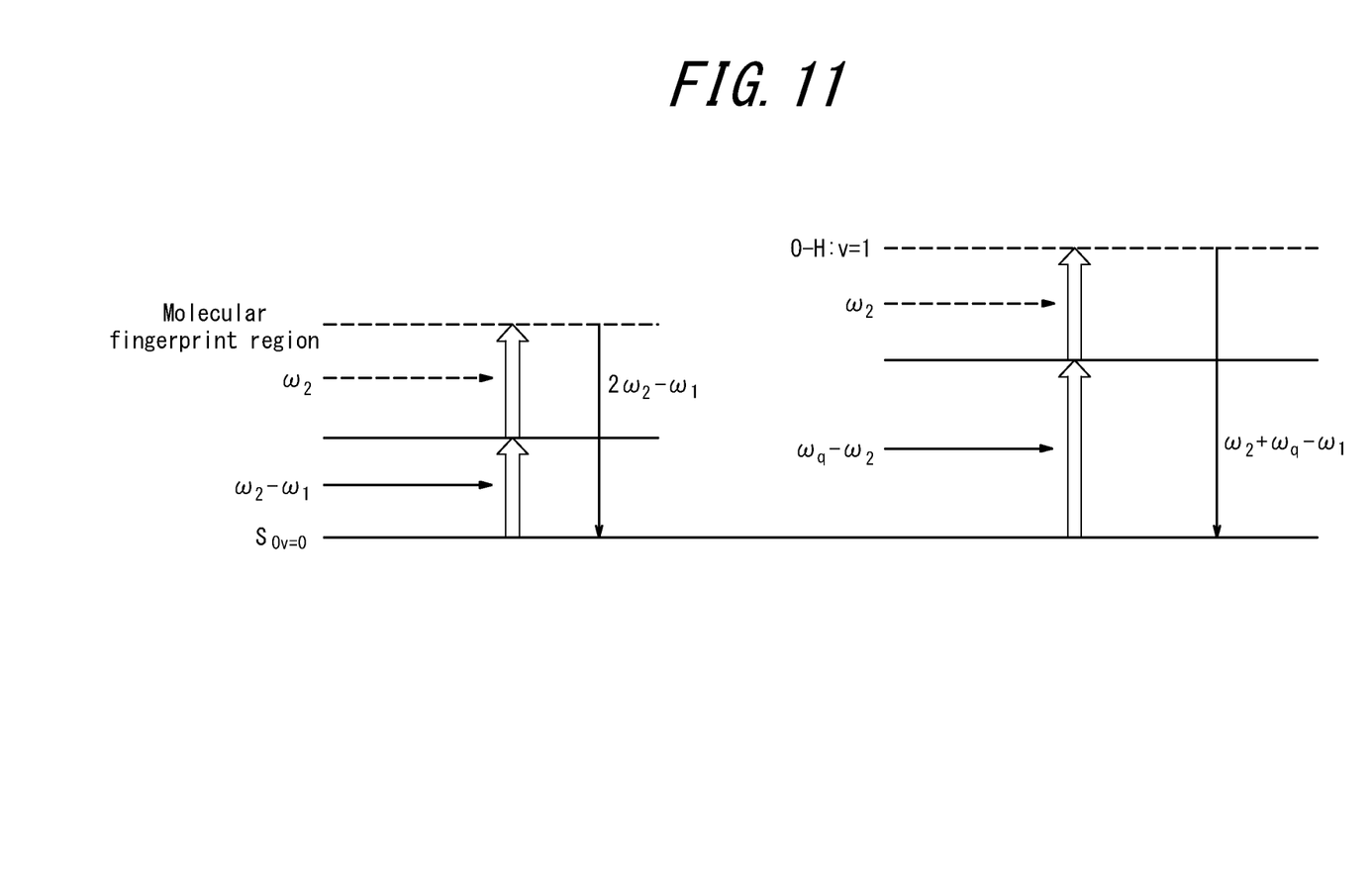
FIG. 11 is an excitation diagram for the super-resolution microscope of FIG. 1.

FIG. 11 illustrates the excitation process of a molecule with the super-resolution microscope of the present embodiment. In FIG. 11, the $\omega_2$ beam is a beam with a wavelength of 1064 nm (wavenumber 9398 cm$^{-1}$) and is a seed beam of the photonic crystal fiber 22 split by the multi-bandpass filter 12. To induce vibration of the "molecular fingerprint region", a beam with a wavenumber approximately 1000 cm$^{-1}$ lower than the $\omega_2$ beam, such as a beam with a wavenumber of 7898 cm$^{-1}$, is used as the $\omega_1$ beam. This $\omega_1$ beam corresponds to a beam with a wavelength of 1190 nm split by the multi-bandpass filter 12.

As illustrated in FIG. 11, when the $\omega_1$ beam and the $\omega_2$ beam are irradiated on the sample S, a vibration state is generated in the molecular fingerprint region due to the difference frequency beam ($\omega_2-\omega_1$) of the $\omega_1$ beam and the $\omega_2$ beam. The difference frequency beam emitted from this state combines with the $\omega_2$ beam so that a new sum frequency beam ($2\omega_2-\omega_1$) is generated as a CARS signal of the molecular fingerprint region.

Furthermore, when an $\omega_q$ beam with a wavenumber of 12598 cm$^{-1}$ (wavelength 794 nm) is irradiated on the sample 5, a combination scheme of these beams changes significantly at this moment. Specifically, molecular vibration of the OH group is induced by the difference frequency beam ($\omega_q-\omega_2$) of the $\omega_2$ beam and the $\omega_q$ beam. The frequency of the OH group generally has a larger optical vibration intensity than the frequency of the molecular fingerprint region, and it is overwhelmingly more likely for a vibration state of the OH group to be generated than a vibration state of the molecular fingerprint region.

In other words, the $\omega_2$ beam couples more easily with the $\omega_q$ beam than the $\omega_1$ beam, and the population of the vibration state of the molecular fingerprint region necessary for generation of the CARS signal of the molecular fingerprint region reduces. Consequently, the signal at the frequency corresponding to the CARS signal ($2\omega_2-\omega_1$) degrades. Instead, the CARS signal at the frequency derived from the OH group ($\omega_2+\omega_q-\omega_1$) increases. This CARS signal corresponds to a beam with a wavenumber of 14098 cm$^{-1}$ and a wavelength of 709 nm.

This means that the CARS process derived from an OH group becomes the suppression process, and the $\omega_q$ beam functions as quench light. Quantitatively, the nonlinear susceptibility of the suppression process is greater than the nonlinear susceptibility of the CARS process in the molecular fingerprint region, i.e. the signal generation process. Low-intensity quench light can therefore suppress the signal generation process. Consequently, options for light source devices can be increased, and a spectroscopically high S/N ratio can be secured.

In a band with a wave number of 2500 cm$^{-1}$ or higher, the oscillator strength is high for a CH group, an NH group, and the like as well as for an OH group, and a resonance band in which the nonlinear susceptibility of the CARS process is high exists. The CARS process derived from these groups can therefore be used as an efficient suppression process. Additionally, these chemical groups are abundantly included in the molecular structure of a variety of molecules, making it possible to suppress the signal generation process more efficiently.

In the present embodiment, the $\omega_1$ beam and $\omega_2$ beam are obtained from light emitted by the super continuum light source 11. Here, the super continuum light source 11 can generate high-brightness coherent light in a continuous wavelength band. Hence, illuminating quench light over such a broad band can simultaneously generate various suppression processes, allowing the signal generation process to be suppressed even more effectively.

Second Embodiment

Figure 12:
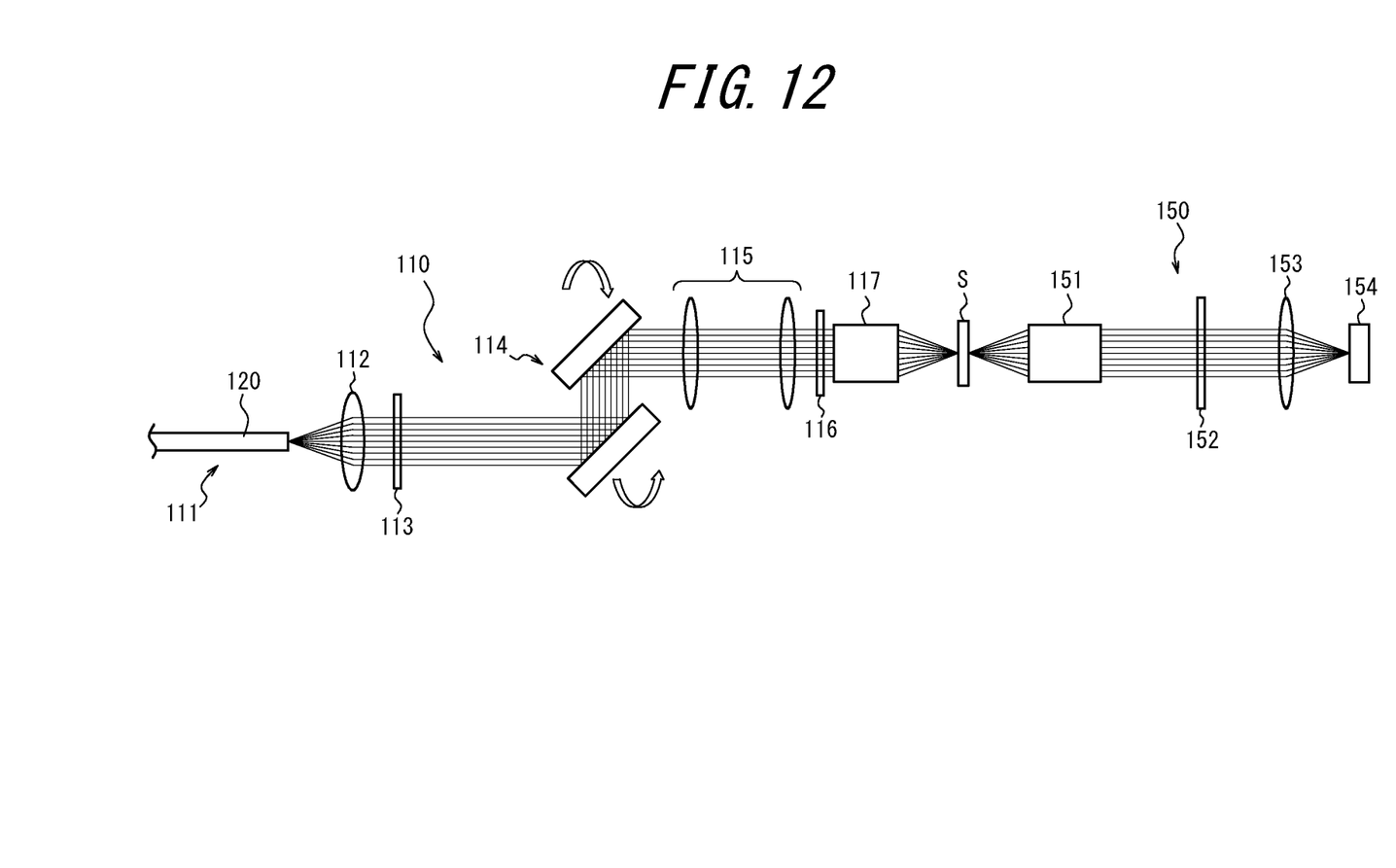
FIG. 12 illustrates the schematic configuration of a super-resolution microscope according to a second embodiment.

FIG. 12 illustrates the schematic configuration of a super-resolution microscope according to the second embodiment of the present disclosure. As in FIG. 2, the super-resolution microscope illustrated in FIG. 12 constitutes a CARS microscope and includes an illuminator 110 and a detection unit 150. The illuminator 110 includes a light source 111, a collimator lens 112, a multi-bandpass filter 113, a galvano mirror optical system 114, a pupil projection lens 115, a spatial modulator 116, and an objective lens 117.

The light source 111 includes a plurality of super continuum light sources. In principle, a super continuum light source extracts white light, from a fiber end face, generated in a photonic crystal fiber by a nonlinear optical effect and extracts an illumination beam of a required wavelength with a dispersive optical element (such as a diffraction grating or a spectral filter). In the present embodiment, the photonic crystal fiber tips of a plurality of super continuum light sources are bundled together to form a multi-fiber bundle 120. Using the emission tip of the multi-fiber bundle 120 as a plurality of light source points, a white light multibeam is emitted from the plurality of light source points.

The white light multibeam emitted from the plurality of light source points of the multi-fiber bundle 120 is converted to a coaxial parallel beam by the collimator lens 112 and is then incident on the multi-bandpass filter 113. From the incident white light, the multi-bandpass filter 113 extracts a three-color illumination beam composed of an $\omega_1$ beam and $\omega_2$ beam, which become a first illumination beam, and an $\omega_q$ beam (quench light), which becomes a second illumination beam.

The three-color illumination beam extracted from the multi-bandpass filter 113 is deflection scanned in two dimensions by the galvano mirror optical system 114, passes through the pupil projection lens 115 and the spatial modulator 116, and is focused on a sample S as multi-spots by the objective lens 117. The spatial modulator 116 is, for example, configured as illustrated in FIG. 3 and modulates the polarization state or the phase state so that, relative to each of the multi-spots formed on the sample S, the $\omega_1$ beam and the $\omega_2$ beam are focused in a Gaussian state, and the quench light is focused in a hollow state. As a result, in each of the multi-spots formed on the sample S, the minimum in the light intensity at the hollow center of the quench light matches the maximum in the light intensity of the $\omega_1$ beam and the $\omega_2$ beam.

The detection unit 150 includes a collector lens 151, a spectral filter 152, a focusing lens 153, and a two-dimensional detector 154. The collector lens 151 collects the CARS beam, which is forward scattered light from the multi-spots on the sample S, and converts the CARS beam to a parallel beam. From the CARS beam converted to a parallel beam by the collector lens 151, a desired wavelength component is extracted by the spectral filter 152 and is focused by the focusing lens 153 as multi-spots on the two-dimensional detector 154. The two-dimensional detector 154 may be configured using a highly sensitive charge coupled device (CCD) sensor, for example, that has a greater number of pixels than the number of multi-spots formed on the sample S.

According to the present embodiment, the multi-spots formed on the sample S are scanned by the galvano mirror optical system 114 in two dimensions within the converging surface of the objective lens 117, and the CARS beam from the multi-spots is detected by the two-dimensional detector 154. Therefore, the sample S can be measured at ultrahigh speed and at super resolution, allowing live observation of biological phenomena.

In the present embodiment, the $\omega_1$ beam, the $\omega_2$ beam, and the quench light are obtained using a super continuum light source, allowing the sample S to be illuminated efficiently. Moreover, the quench light extracted from the light emitted by the super continuum light source is spatially modulated by the spatial modulator 116, which allows a good hollow spot to be formed on the sample S even when the quench light has a broad band.

Figure 13A:
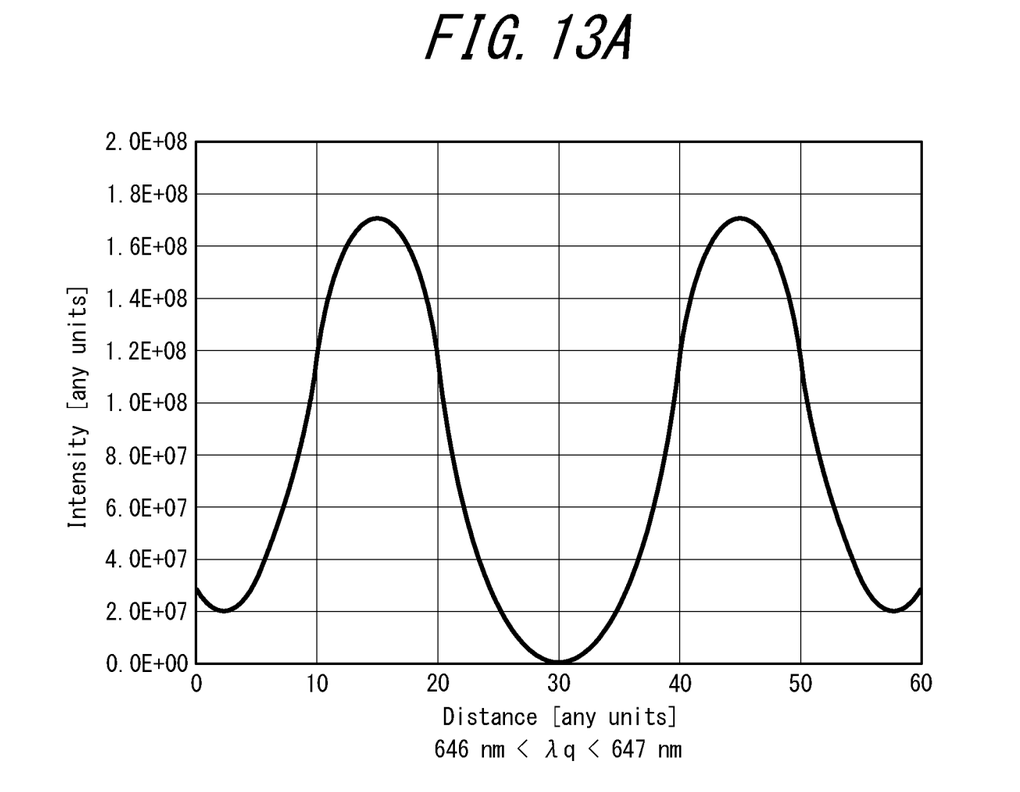
FIG. 13A illustrates the intensity distribution of a concentrated light pattern on the focal plane of quench light when using a line-oscillation laser beam.
Figure 13B:
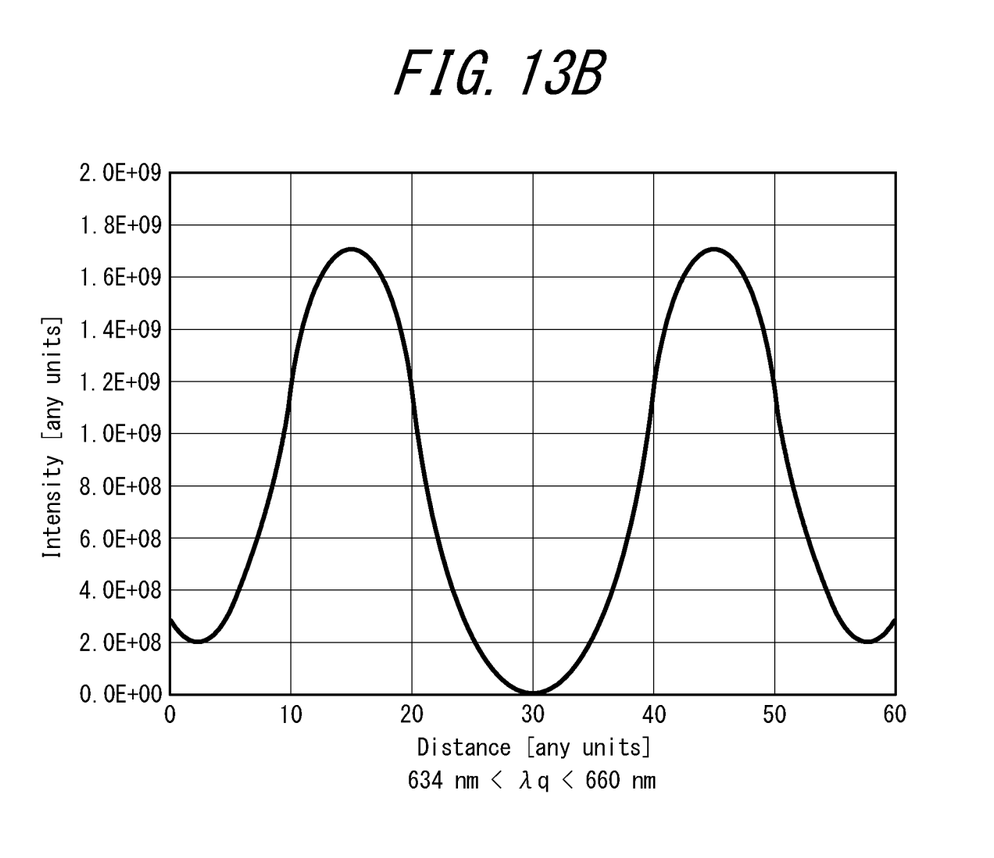
FIG. 13B illustrates the intensity distribution of a concentrated light pattern on the focal plane of quench light when using a white laser beam from a super continuum light source.

FIG. 13A illustrates the intensity distribution of a concentrated light pattern on the focal plane fir quench light when using a line-oscillation laser beam. FIG. 13B illustrates the intensity distribution of a concentrated light pattern on the focal plane for quench light when using a white laser beam from a super continuum light source. FIG. 13A illustrates the case of the wavelength $\lambda_q$ of the quench light satisfying 646 nm<$\lambda_q$<647 nm. FIG. 13B illustrates the case of the central wavelength of the wavelength $\lambda_q$ being 647 nm and the bandwidth being approximately 30 nm to satisfy 634 nm<$\lambda_q$<660 nm. Both FIG. 13A and FIG. 13B illustrate simulation results for modulating with a spatial modulator configured as illustrated in FIG. 4 and focusing light with a common objective lens.

As is clear from FIG. 13B, the intensity at the central portion of the quench light focused on the focal plane is zero even when using broad band quench light split from a white laser beam emitted from a super continuum light source. Accordingly, a super continuum light source can be suitably used as the quench light of a super-resolution microscope, and the sample S can efficiently be irradiated by taking advantage of the characteristics of the super continuum light source.

The present disclosure is not limited to the above embodiments, and a variety of changes and modifications may be made. For example, in the first embodiment, the two-dimensional scanning in the xy-directions of the sample S may be performed using a gal vano mirror optical system as in the second embodiment. In the second embodiment, a three-dimensional super-resolution microscopic image may be obtained by displacing the sample S in the direction of the optical axis of the objective lens 117. In this case, the sample S may be mounted on a sample stage displaceable in three dimensions, as in the first embodiment, instead of using the galvano mirror optical system 114.

In the above embodiments, since illumination beams of three colors are focused on the sample, generation processes and the like of a variety of second-order and/or third-order sum frequencies resulting from combinations of these illumination beams also compete. In the above embodiments, such generation processes and the like of second-order and/or third-order sum frequencies can also be used to suppress the CARS beam, thereby allowing broader super-resolution microscopy. In the present disclosure, a signal beam generated by a fourth-order or fifth-order nonlinear effect or the like can also be effectively applied if the competition process can be artificially induced by quench light with a different wavelength than the above wavelength.

In the above embodiments, a three-color laser beam, including quench light, is used to take advantage of the nonlinear optical process of a CARS process. When taking advantage of the nonlinear optical process of an SHG photon generation process, for example, super-resolution microscope observation can be performed using a two-color laser beam, with the first illumination beam and the second illumination beam each being one color. Accordingly, the nonlinear optical process may, for example, be generated in the present disclosure with any of the following processes: a second-order nonlinear optical process, a third-order nonlinear optical process, a fourth-order nonlinear optical process, and a fifth-order nonlinear optical process.

The second-order nonlinear optical process includes, for example, any of second harmonic generation (SHG), sum frequency generation (SFG), difference frequency generation (DPG), and an optical parametric process.

The third-order nonlinear optical process includes, for example, any of third harmonic generation (THG), third-order sum frequency generation (TSFG), coherent anti-Stokes Raman scattering (CARS), stimulated Raman scattering (SRS) (stimulated Raman gain (SRG), stimulated Raman loss (SRL)), optical Kerr effect (OKE), Raman induced Kerr effect (RIME), stimulated Rayleigh scattering, stimulated Brillouin scattering (SBS), stimulated Kerr scattering, stimulated Rayleigh-Bragg scattering, stimulated Mie scattering, self phase modulation (SPM), cross phase modulation (XPM), two-photon absorption, optical-field induced birefringence, and electric-field induced SHG.

The fourth-order nonlinear optical process includes, for example, four-wave mixing (FWM).

The fifth-order nonlinear optical process includes, for example, any of two-photon excitation fluorescence (TPEF), hyper-Raman scattering, hyper-Rayleigh scattering, and coherent anti-Stokes hyper-Raman scattering.

In the present disclosure, a CARS beam that is generated as a first nonlinear optical process and becomes an image signal has been described, but beams generated by any other nonlinear optical process can also be used. For example, a stimulated Raman light wave generated on the long wavelength side of a CARS beam carries equivalent information on the inside of a sample as the CARS beam. An ultrahigh-precision lock-in amplifier that classifies weak signals includes a large background component and is difficult to use in terms of the S/N ratio. In recent years, however, the development of electronics technology has made use of such lock-in amplifiers possible, and minute regions of transparent biological samples have successfully been visualized (see Y. Ozeki, Y. Kitagawa, K. Sumimura, N. Nishizawa, W. Umemura, S. Kajiyama, K. Fukui, and K. Itoh, "Stimulated Raman scattering microscope with shot noise limited sensitivity using subharmonically synchronized laser pulses", OPTICS EXPRESS, Vol. 18, No. 13, pp. 13708-13719 (2010)). The present disclosure can be applied to these nonlinear optical processes. A two-photon process often used in laser scanning microscopes can also be introduced.

The invention claimed is:

1. A super-resolution microscope comprising:
an illuminator configured to irradiate a plurality of illumination beams of different wavelengths through an objective lens onto a sample while causing at least a portion of the plurality of illumination beams to overlap spatially and temporally; and
a detector configured to detect a signal beam generated by the sample as a result of irradiation of the sample with the plurality of illumination beams; wherein
the plurality of illumination beams comprises a first illumination beam that induces a first nonlinear optical process with respect to the sample and a second illumination beam that induces a second nonlinear optical process that suppresses the first nonlinear optical process; and
a nonlinear susceptibility of the second nonlinear optical process is greater than a nonlinear susceptibility of the first nonlinear optical process.

2. The super-resolution microscope of claim 1, wherein the second illumination beam has a shorter wavelength than the first illumination beam.

3. The super-resolution microscope of claim 2, wherein the first illumination beam and the second illumination beam have different intensity distributions on a converging surface of the objective lens.

4. The super-resolution microscope of claim 3, wherein the second illumination beam has a minimum in the intensity distribution on the converging surface.

5. The super-resolution microscope of claim 4, wherein the first illumination beam has a maximum in the intensity distribution on the converging surface.

6. The super-resolution microscope of claim 5, wherein each of the first nonlinear optical process and the second nonlinear optical process comprises any of a second-order nonlinear optical process, a third-order nonlinear optical process, a fourth-order nonlinear optical process, and a fifth-order nonlinear optical process;
the second-order nonlinear optical process is any of
second harmonic generation (SHG),
sum frequency generation (SFG),
difference frequency generation (DM), and
an optical parametric process;
the third-order nonlinear optical process is any of
third harmonic generation (THG),
third-order sum frequency generation (TSFG),
coherent anti-Stokes Raman scattering (CARS),
stimulated Raman scattering (SRS) (stimulated Raman gain (SRG), stimulated Raman loss (SRL)),
optical Kerr effect (OKE),
Raman induced Kerr effect (RIKE),
stimulated Rayleigh scattering,
stimulated Brillouin scattering (SBS),
stimulated Kerr scattering,
stimulated Rayleigh-Bragg scattering,
stimulated Mie scattering,
self phase modulation (SPM),
cross phase modulation (XPM),
two-photon absorption,
optical-field induced birefringence, and
electric-field induced SHG;
the fourth-order nonlinear optical process is four-wave mixing (FWM); and
the fifth-order nonlinear optical process is any of
two-photon excitation fluorescence (TPEF),
hyper-Raman scattering,
hyper-Rayleigh scattering, and
coherent anti-Stokes hyper-Raman scattering.

7. The super-resolution microscope of claim 6, wherein
the first illumination beam and the second illumination beam are coherent beams; and
the illuminator comprises a spatial modulator configured to modulate a phase or a spatial distribution of an electrical field vector of the second illumination beam.

8. The super-resolution microscope of claim 7, wherein the maximum of the first illumination beam and the minimum of the second illumination beam overlap coaxially at the converging surface.

9. The super-resolution microscope of claim 8, wherein the detector detects forward scattered light, or light generated in a nonlinear optical process, from the sample as the signal beam.

10. The super-resolution microscope of claim 9, wherein the second nonlinear optical process comprises a lower order nonlinear optical process than the first nonlinear optical process.

11. The super-resolution microscope of claim 1, wherein the first illumination beam comprises illumination beams of at least two colors of different wavelengths.

* * * * *